US009668752B2

(12) United States Patent
Rothenwaender et al.

(10) Patent No.: US 9,668,752 B2
(45) Date of Patent: Jun. 6, 2017

(54) METHOD FOR CONTROLLING AND/OR REGULATING A COMPRESSED-GAS-OPERABLE MEDICAL DRIVE DEVICE AND SUCH A DRIVE DEVICE

(71) Applicant: W&H Dentalwerk Bürmoos GmbH, Bürmoos (AT)

(72) Inventors: Michael Rothenwaender, Lamprechtshausen (AT); Karlheinz Eder, Lamprechtshausen (AT); Christian Pruckner, Vienna (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 693 days.

(21) Appl. No.: 14/063,936

(22) Filed: Oct. 25, 2013

(65) Prior Publication Data

US 2014/0120496 A1    May 1, 2014

(30) Foreign Application Priority Data

Oct. 25, 2012  (EP) ..................................... 12189921

(51) Int. Cl.
*A61C 1/05*  (2006.01)
*A61B 17/16*  (2006.01)
(Continued)

(52) U.S. Cl.
CPC ...... *A61B 17/1624* (2013.01); *A61B 17/1626* (2013.01); *A61B 17/1628* (2013.01);
(Continued)

(58) Field of Classification Search
CPC ... A61C 1/05; A61B 17/1624; A61B 17/1626; A61B 17/1644
(Continued)

(56) References Cited

U.S. PATENT DOCUMENTS 3,386,702 A  *  6/1968  Krzyszczuk ............. A61C 1/05
                                              415/123
3,865,505 A  *  2/1975  Flatland ................... A61C 1/05
                                              415/146
(Continued)

FOREIGN PATENT DOCUMENTS

DE     28 39 632      3/1980
EP     1 733 694      12/2006
(Continued)

OTHER PUBLICATIONS

Office Action from the Japanese Patent Office for Japanese Patent Application No. 2013-221110, dated Aug. 19, 2014.
(Continued)

*Primary Examiner* — Nathaniel Chukwurah
(74) *Attorney, Agent, or Firm* — Klarquist Sparkman, LLP

(57) ABSTRACT

Methods for controlling and/or regulating of a compressed-gas-operable medical or dental drive device and a control and/or regulating device for performing such methods are described. In one method according to a first embodiment, a rotor of the drive device is operated at an essentially constant rotational speed ($n_1$) by adjusting the gas pressure and/or the flow rate of the compressed gas through a valve and the rotational speed is reduced on reaching a pressure value ($p_2$) of the compressed gas which is lower than the maximum gas pressure ($p_{max}$) of the compressed gas. In the case of a method according to a second embodiment, the gas pressure of the compressed gas and the rotational speed of the rotor are altered on reaching a rotational speed limit value ($n_2$, $n_3$) of the rotor by adjusting the valve.

18 Claims, 4 Drawing Sheets

(51) Int. Cl.
*A61C 1/00* (2006.01)
*A61C 1/12* (2006.01)
*A61B 17/00* (2006.01)

(52) U.S. Cl.
CPC ............ *A61C 1/003* (2013.01); *A61C 1/0023* (2013.01); *A61C 1/0038* (2013.01); *A61C 1/0061* (2013.01); *A61C 1/05* (2013.01); *A61C 1/12* (2013.01); *A61B 2017/00544* (2013.01)

(58) Field of Classification Search
USPC ...... 173/1, 46, 199; 433/98, 132, 215; 606/1
See application file for complete search history.

(56) References Cited

U.S. PATENT DOCUMENTS

| | | | | |
|---|---|---|---|---|
| 4,278,427 A * | 7/1981 | Lingenhole | .......... | A61C 1/0007 173/177 |
| 4,493,643 A | 1/1985 | Tachibana | | |
| 4,723,911 A | 2/1988 | Kurtz | | |
| 5,782,634 A * | 7/1998 | Lingenhole | ............ | A61C 1/052 415/904 |
| 7,192,248 B2 * | 3/2007 | Helvey | .................... | B23Q 5/06 415/202 |
| 2008/0102418 A1 * | 5/2008 | Krieger | ................ | A61C 1/0015 433/98 |
| 2008/0145817 A1 * | 6/2008 | Brennan | ................ | A61C 1/003 433/98 |

FOREIGN PATENT DOCUMENTS

| | | |
|---|---|---|
| JP | S58103448 | 6/1983 |
| JP | S62172943 | 7/1987 |
| JP | 3025054 U | 6/1996 |
| JP | 2011-241092 | 12/2011 |
| JP | 2012011068 A | 1/2012 |

OTHER PUBLICATIONS

Office Action for Japanese Patent Application No. 2015-225363 (mailed Aug. 23, 2016).

* cited by examiner

METHOD FOR CONTROLLING AND/OR REGULATING A COMPRESSED-GAS-OPERABLE MEDICAL DRIVE DEVICE AND SUCH A DRIVE DEVICE

CROSS REFERENCE TO RELATED APPLICATION

The present application claims priority from pending European Patent Application No. 12189921.5, filed Oct. 25, 2012, which is incorporated herein by reference.

BACKGROUND

Field

The present invention relates to methods for controlling and/or regulating a compressed-gas-operable medical or dental drive device and such a drive device.

Description of Prior Art

Known methods for controlling and/or regulating a compressed-gas-operable medical, in particular dental, drive device are diagrammed schematically in FIGS. 1 and 2 on the basis of torque/rotational speed diagrams. The two figures each show a torque/rotational speed diagram of a drive device that can be induced to rotate, in particular of a rotor that can be acted upon by compressed gas and/or a tool-holding device connected thereto. The rotational speed (n) of the drive device is plotted on the abscissa and the torque (M) is plotted on the ordinate. In addition, the diagrams show as examples a few pressure curves (straight lines $p_1$, $p_2$, $p_{max}$), each representing a gas pressure value of the compressed gas. The pressure value $p_{max}$ is the highest available pressure gas value, wherein the drive device usually has a valve that limits the gas pressure to the maximum value $p_{max}$. A rotational speed $n_1$, $n_2$, $n_{max}$ correlates with each gas pressure value $p_1$, $p_2$, $p_{max}$, where $n_{max}$ stands for the highest achievable rotational speed.

It should be pointed out that the diagrams in FIGS. 1 and 2 as well as all additional diagrams are considered fundamentally in the direction of increasing torque. The description is also worded accordingly. However, the invention is of course not limited to this approach, but instead clearly also includes a characteristic in the direction of decreasing torque, as also shown in the diagrams.

FIG. 1 shows a torque/rotational speed diagram of a known method for controlling a compressed-gas-operable medical or dental drive device. This drive device has a control valve, which can be operated by a user through an adjusting device that can be operated by foot (referred to below as a foot control) and is designed to control the gas pressure and/or the flow rate of the compressed gas according to the foot control position and thus to determine the rotational speed of the rotor. If the user selects the pressure value $p_1$ as the desired pressure in idling, for example, by operating the foot control and thus operating the control valve, then the rotor will rotate at the rotational speed $n_1$, and the situation is similar for each additional selectable pressure and the respective rotational speed see, for example, the pressure value $p_2$ and the rotational speed $n_2$ as well as the maximum pressure value $p_{max}$ and the maximum rotational speed $n_{max}$. Correspondingly, the torque of the drive device or the torque of the rotor is at least almost zero in idling accordingly. "In idling" means that a tool held in the tool-holding device does not come in contact with a part that is to be worked, in particular a body tissue such as a tooth, a bone or a replacement material, and therefore the tool is not applied by a load.

If the user contacts a part that is to be processed with the tool or if the user applies a load to the tool, then, depending on the magnitude of the load, the rotational speed declines according to the course of the straight lines assigned to the respective pressure value $p_1$, $p_2$, $p_{max}$ and the torque increases accordingly. The torque reaches its maximum value when the rotational speed is zero.

Work on a body tissue thus comprises a permanent direct or indirect change in rotational speed, torque and gas pressure by the user, for example, by means of the foot control, exclusively on the basis of the user's perception, for example, the visually observed removal of material or the speed of rotation of the tool, the force to be applied by hand to the part to be processed or the frequency of the drive device. Therefore the user can achieve the various settings for the rotational speed, the torque and/or the gas pressure desired for different treatments, for example, only approximately on the basis of his senses.

FIG. 2 shows a torque/rotational speed diagram of a second known method for regulating the rotational speed of a compressed-gas-operable medical or dental drive device. The method of FIG. 2 corresponds to the method of FIG. 1, but regulation is provided when the rotor reaches a predetermined rotational speed value $n_3$. The rotational speed value $n_3$ defines a rotational speed limit value which is not exceeded and/or at which is regulated by regulating the supply of compressed gas by means of a control valve. When the user increases the gas pressure or flow rate of the compressed gas, the torque of the rotor or the torque of the tool thereby driven is increased, optionally until reaching the maximum gas pressure $p_{max}$. The torque increases further if the load on the tool increases further but the rotational speed then declines accordingly (see the rotational speed/torque characteristic line emphasized in FIG. 2). Such a method is known from the patent application US 2008/0145817 A1, for example. Thus, during operation a defined course for a rotational speed value ($n_3$) or a predetermined ratio of rotational speed, torque and gas pressure is available to the user, but for all rotational speeds below this predetermined rotational speed value ($n_3$), the user must again rely on his senses, as described above with regard to FIG. 1.

SUMMARY

One object of the present application is therefore to create a method for controlling and/or regulating a compressed-gas-operable medical or dental drive device, a corresponding control and/or regulating device and a corresponding drive device, which will not have the disadvantages mentioned above. This method, the control and/or regulating device and the drive device should in particular be designed so that they preferably offer the user more predefined and/or freely selectable treatment options, so that precisely defined operating conditions adapted to different treatments in particular and actually adjusted to the drive device are made available for the user.

According to a first embodiment, this object is achieved by a method for controlling and/or regulating a compressed-gas-operable medical or dental drive device, in which the rotor is operated at an essentially constant rotational speed, at least within a limited load range, by adjusting the gas pressure and/or the flow rate of the compressed gas through the valve and the rotational speed is reduced on reaching a pressure value of the compressed gas, which is lower than the maximum gas pressure of the compressed gas.

It is thus possible for the user to keep the rotational speed essentially constant at first, as is known, but to obtain a reduction in the rotational speed in contrast with the state of the art, on reaching a pressure value of the compressed gas which is lower than the maximum gas pressure $p_{max}$.

According to a second embodiment, a method for controlling and/or regulating a compressed-gas-operable medical or dental drive device is provided in which the gas pressure of the compressed gas and the rotational speed of the rotor are adjusted by adjusting the valve on reaching a rotational speed limit value of the rotor.

In contrast with the state of the art, in this second embodiment, two parameters, namely the gas pressure of the compressed gas and the rotational speed of the rotor, are adjusted (at the same time).

With the two methods mentioned above, the gas pressure value of the compressed gas and/or the value of the essentially constant rotational speed and/or the rotational speed limit value is/are adjustable by a user. An operating device which is therefore provided for the user is connected to the drive device or is designed as part of the drive device. This operating device may be designed for selecting preset values and/or for continuous selection at least within a limited range, for example. For adjusting the selected gas pressure value of the compressed gas and/or of the selected essentially constant rotational speed value and/or of the rotational speed limit value, the operating device is connected to a control and/or regulating device and/or to an actuator element, for example, the valve. The operating device comprises for example, at least one pushbutton, a turn knob or a touchscreen. The operating device is operable by hand or foot, for example.

With the two methods described above, the drive device has at least one rotor, a tool-holding device connected to the rotor and a valve for adjusting the gas pressure and/or the flow rate of the compressed gas, for example, a control valve or a regulating valve, preferably a proportional valve, in particular a solenoid valve. In addition, the drive device can be supplied with a compressed gas at a maximum gas pressure from a compressed gas source in order to induce a rotational movement of the rotor. The compressed gas source is preferably designed as a compressed air source, supplying compressed air to the drive device.

The two methods described above advantageously offer the user a much larger number of treatment options in comparison with the state of the art, preferably for different treatments. In particular precisely defined ratios, characteristics or combinations of rotational speed values, torque values and gas pressure values that are controlled or regulated or monitored and are maintained during the treatment (continuously) are made available to the user. In addition, the user advantageously has the option of defining or selecting precise settings of the rotational speed, the torque and the gas pressure and/or precise settings of desired ratios, courses or combinations of these parameters.

The method for controlling and/or regulating a compressed-gas-operable medical or dental drive device preferably includes a lower limit of the rotational speed below which the method for controlling and/or regulating is not performed, wherein the lower limit of the rotational speed is $>0 \text{ s}^{-1}$. The lower limit of the rotational speed is either freely selectable by the user or is defined as an invariable parameter. The lower limit of the rotational speed advantageously offers the user an additional option for individualization of treatments.

According to a third embodiment, a method for controlling and/or regulating a compressed-gas-operable medical or dental drive device is provided, in which at least one of the following parameters is freely selectable by the user at least within a predefined range when the drive device or the rotor is not being supplied with compressed gas or the drive device is not being operated or the rotor is not being rotated: a rotational speed limit value of the rotor that is lower than the maximum rotational speed $n_{max}$ determined by the maximum gas pressure $p_{max}$, a setpoint rotational speed of the rotor, a gas pressure limit value of the compressed gas (that can be supplied to the rotor), which is lower than the maximum gas pressure ($p_{max}$) available to the drive device and/or a torque value. The drive device comprises a rotor, a tool-holding device connected to the rotor and a valve for adjusting the gas pressure and/or the flow rate of the compressed gas, wherein the drive device can be supplied with compressed gas at a maximum gas pressure from a compressed gas source.

The selection of a value for at least one of these parameters permits individualization of treatments for the user in an advantageous manner.

For selecting a value of at least one of these parameters, an operating device is provided for the user that is designed as part of the drive device or is connected to the drive device. The operating device may be designed for selection of preset values, for example, and/or for a continuous selection at least within a limited range. To set a value, the operating device is connected to a control and/or regulating device, for example, and/or to an actuator element, in particular a valve. The actuator element is designed to induce a change in the rotational speed of the rotor, the setpoint rotational speed of the rotor, the maximum gas pressure of the compressed gas or of the torque, in particular by acting on the compressed gas, for example, through a change in the cross section of a valve opening through which the compressed gas flows. The operating device comprises at least one pushbutton, a turn knob or a touchscreen, for example. The operating device may be operated by hand or by foot, for example.

The methods according to the three embodiments described above can preferably be implemented individually or all of them combined together; in particular the method according to the third embodiment can be combined with the method according to the first embodiment or with the method according to the second embodiment.

According to a fourth embodiment, a method for detecting wear or a defect in at least one part of a drive device is provided, wherein a gas pressure value of the compressed gas for driving the drive device, in particular the rotor, is or will be preset in this method, the drive device, in particular the rotor, being induced to rotate by applying compressed gas at the preset gas pressure value; the rotational speed of the drive device, in particular the rotor, being determined by a rotational-speed-measuring device and transmitted to a control and/or regulating device; the measured rotational speed value being compared by the control and/or regulating device with a rotational speed setpoint value, wherein the rotational speed setpoint value is defined by a rotational speed that is assigned to the predetermined gas pressure value, and if the measured rotational speed value is not equal to the rotational speed setpoint value or if it is outside of a tolerance range of the rotational speed setpoint value, the operation of the drive device is prevented and/or a display for informing the user is activated.

The method for detecting wear or a defect is preferably performed while idling or in the absence of a load on the drive device, in particular without a load on a tool driven by the drive device or without the drive device or a tool driven by the drive device being in contact with an object that is to be processed. The rotational speed setpoint value is preferably formed by the idling rotational speed that correlates with the predefined gas pressure value. For example, the tolerance range that includes the rotational speed setpoint value covers ±5% or ±10% of the rotational speed setpoint value.

The method for detecting wear or a defect makes it possible in particular to detect worn or defective bearings which support the rotor and/or the tool-holding device in particular, or objects in the drive device or components of the drive device which are loose or have become loosened, and are in contact with a rotating component of the drive device, in particular the rotor and/or the tool-holding device.

The operation of the drive device is suppressed, for example, by suppressing the supply of compressed gas to the drive device, in particular to the rotor, for example, by completely cutting off a valve in the compressed gas supply for the drive device. The display for informing the user comprises, for example, a visual signal generator, in particular a light source, an acoustic signal generator or a tactile signal generator.

According to one embodiment, a control and/or regulating device is provided, designed to perform at least one of the methods described above for controlling and/or regulating a compressed-gas-operable medical or dental drive device and/or of the method for detecting wear or a defect in at least one part of a drive device. The control and/or regulating device is preferably electrically operated and comprises a microcontroller in particular. The control and/or regulating device is preferably operatively connected to the display for informing the user as described above. The control and/or regulating device is preferably operatively connected to the operating device described above. The control and/or regulating device is preferably designed as part of the medical or dental drive device or is operatively connected to the medical or dental drive device.

According to one embodiment, the medical or dental drive device in addition to the aforementioned control and/or regulating device also comprises a rotor that can be induced into rotation by the compressed gas, a tool-holding device connected to the rotor, a rotational-speed-measuring device for measuring the rotational speed of the rotor and/or of the tool-holding device, a valve for adjusting the gas pressure and/or the flow rate of the compressed gas and preferably a device for determining the gas pressure of the compressed gas wherein the control and/or regulating device is operatively connected to the rotational-speed-measuring device, preferably connected to the device for determining the gas pressure and to the valve, so that measured data on the rotational speed and optionally also measured data on the gas pressure can be transmitted to the control and/or regulating device, and the valve can be operated by the control and/or regulating device to adjust the gas pressure and/or the flow rate of the compressed gas on the basis of the transmitted measured data on the rotational speed and/or optionally the measured data on the gas pressure.

The drive device preferably comprises a handpiece or a contra-angle handpiece in which at least the rotor or turbine and the tool-holding device are provided. Each of the other components mentioned above (the control and/or regulating device(s), the rotational-speed-measuring device, the valve, the device for determining the gas pressure) may be provided in the handpiece or in the contra-angle handpiece or outside of the handpiece or the contra-angle handpiece, for example, in a coupling device or a conduit for connecting the handpiece or the contra-angle handpiece to the compressed gas source or in a supply unit. The valve for adjusting the gas pressure and/or the flow rate of the compressed gas comprises, for example, a control or regulating valve, in particular a solenoid valve. The rotational-speed-measuring device is designed, for example, as an inductive, capacitive or optical rotational-speed-measuring device. The device for determining the gas pressure is designed, for example, as a microphone, as a capacitive, inductive or piezoelectric sensor. Alternatively it is also possible to determine the gas pressure indirectly, preferably by detecting an actuating variable of the valve for adjusting the gas pressure and/or the flow rate of the compressed gas, for example, the position of the valve body or by determining the value of a control or regulating signal, for example, the amperage, applied to the valve.

According to one embodiment, the drive device comprises at least one actuator element that can be operated by a user for defining at least one of the following parameters: a rotational speed limit value of the rotor, which is lower than the maximum rotational speed determined by the maximum gas pressure, a setpoint rotational speed of the rotor, a gas pressure limit value of the compressed gas, which is lower than the maximum gas pressure ($p_{max}$) available to the drive device, of a torque (limit) value. The actuator element is connected to an operating device as described above, for example.

The methods described herein comprise automated or electronically controlled or regulated, in particular controlled or regulated by a microcontroller, methods or steps.

These and other embodiments will be described below with reference to the following drawings.

DETAILED DESCRIPTION

FIGS. 3-7 show torque/rotational speed diagrams of drive devices that can be induced to rotate, in particular of a rotor that can be acted upon by compressed gas and/or a tool-holding device connected thereto. The rotational speed (n) of the drive device is plotted on the abscissa and the torque (M) is plotted on the ordinate. In addition, the diagrams show as examples a few pressure curves (straight lines $p_1$, $p_2$, $p_{max}$), each of which shows a gas pressure value of the compressed gas. The pressure value $p_{max}$ is the highest available compressed gas value, with the drive device usually having a valve that limits the gas pressure of the compressed gas supplied by the compressed gas source to the highest value $p_{max}$ ($p_{max}$ is thus the highest gas pressure available to the drive device or to the rotor of the drive device). A rotational speed $n_1$, $n_2$, $n_{max}$ ($n_{max}$ is the highest rotational speed that can be achieved) correlates with each gas pressure value $p_1$, $p_2$, $p_{max}$. Reference should be made to the fact that all the torque/rotational speed diagrams depicted are approximate schematic diagrams to facilitate an understanding. In particular the pressure curves or the rotational speed-gas pressure curves which are depicted as straight lines are in practice embodied as slightly curved (convex) lines.

Figure 1:
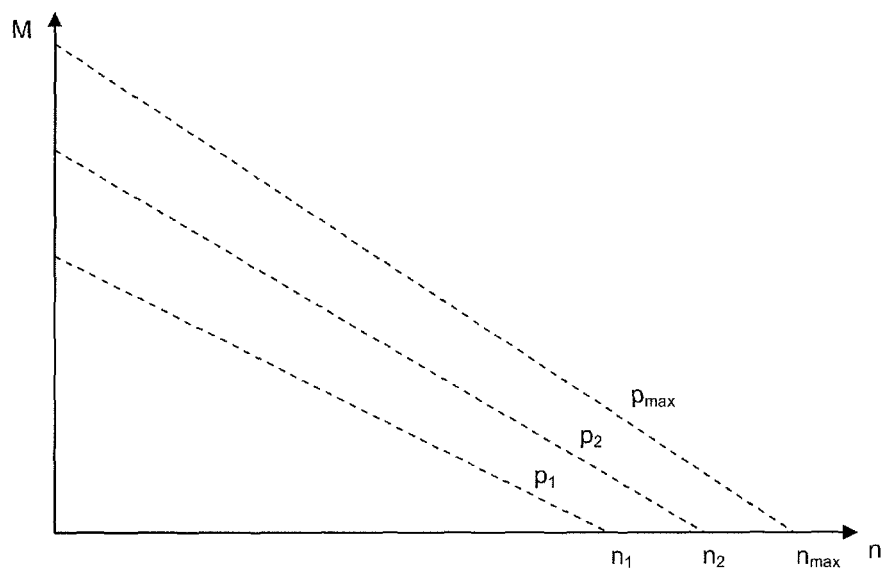
FIGS. 1 and 2 each show a torque/rotational speed diagram of methods known from the state of the art for controlling and/or regulating a compressed-gas-operable medical or dental drive device.
Figure 2:
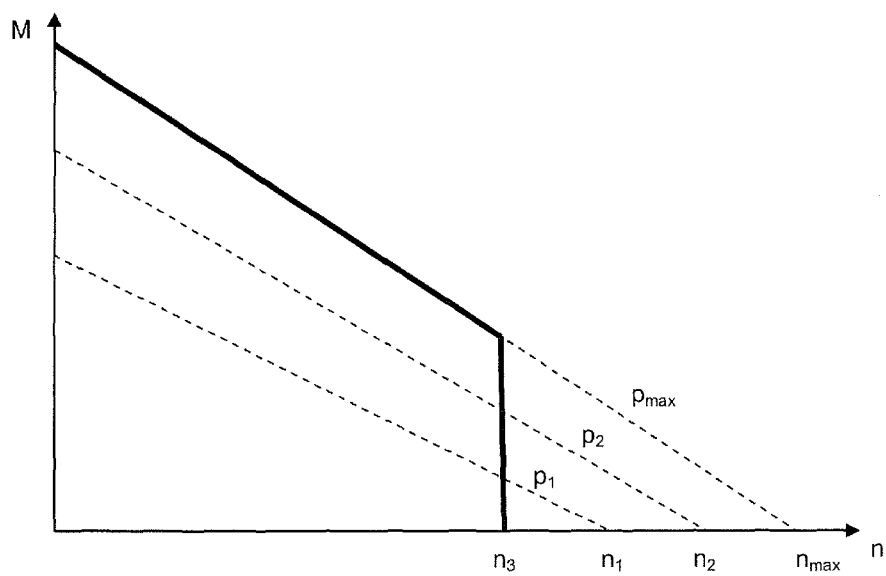
Figure 3:
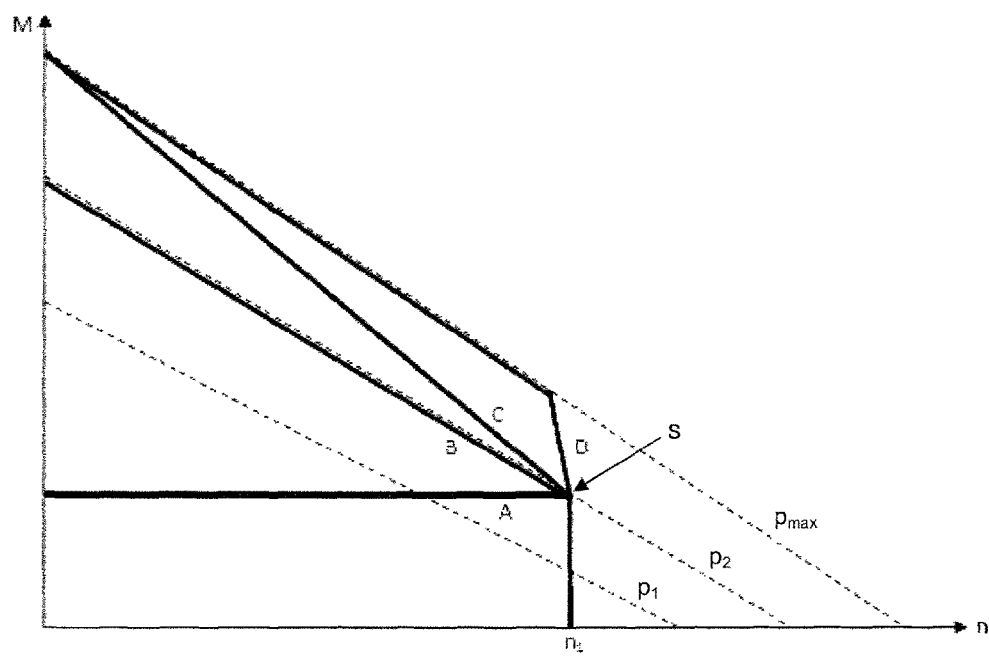
FIGS. 3 and 4 show control and/or regulating characteristics in the form of torque/rotational speed diagrams of methods for controlling and/or regulating a compressed-gas-operable medical or dental drive device.

FIG. 3 shows a torque/rotational speed diagram of a first embodiment of a method for controlling and/or regulating a compressed-gas-operable medical or dental drive device, in which the rotor is operated at an essentially constant rotational speed $n_1$ by adjusting the gas pressure and/or the flow rate of the compressed gas through a valve, at least within a limited load range. On reaching a pressure value $p_2$ of the compressed gas (while the rotor is operated at an essentially constant rotational speed $n_1$), which is lower than the maximum gas pressure $p_{max}$ of the compressed gas, the rotational speed is reduced (in a controlled or regulated process). This method is preferably reversible, so that when the pressure value drops below the pressure value $p_2$, the drive device or the rotor is operated again at an essentially constant rotational speed $n_1$ or with any other control and/or regulating method, for example. Thus, this method in particular is a (reversible) method with two (immediately) successive steps or two steps connected to each other, wherein one step comprises the operating of the rotor at an essentially constant rotational speed $n_1$ and the other step comprises the reduction of the rotational speed.

The pressure value $p_2$ or the combination of the pressure value $p_2$ and the rotational speed $n_1$ thus defines a switching point S, which, on being reached, causes the rotational speed to be reduced. In combination with the reduction in rotational speed, additional changes in values of operating parameters are preferably also possible. For example, with the reduction in rotational speed, the torque remains essentially constant or is increased only slightly; in particular the torque has approximately the same value or only a slightly increased value than it does on reaching the pressure value $p_2$ at which the rotational speed is reduced (see FIG. 3, straight line "A"). This is associated with a reduction in the gas pressure of the pressurized gas driving the rotor. Such a control and/or regulation is/are advantageous with medical or dental precision treatments, for example, or in reworking or in treatments near the dental pulp, in particular in combination with a low rotational speed value $n_1$, which is essentially constant.

Alternatively, the torque increases with a reduction in the rotational speed, in particular increasing substantially. The torque in particular has a higher value, in particular a much higher value, than on reaching the pressure value $p_2$ at which the rotational speed is reduced. Such control and/or regulation is advantageous, for example, in initial medical or dental preparations or working on the dental enamel or dental substitute material, in particular in combination with a high, essentially constant rotational speed value $n_1$. As shown by the straight lines "B", "C" and "D" in FIG. 3, there are again different curves here. Straight line "B" follows essentially the pressure curve $p_2$, i.e., the gas pressure of the compressed gas driving the rotor remains essentially constant. Alternatively, the shape of the straight line "C" shows that the gas pressure of the compressed gas driving the rotor increases, in particular increasing steadily. The increase in the gas pressure may be designed to be such that the gas pressure approaches but does not reach the maximum gas pressure value $p_{max}$ or the gas pressure approaches the maximum compressed gas value $p_{max}$ but reaches it only at very low rotational speeds (see straight line "C" in FIG. 3). Another alternative is represented by the straight line "D" in FIG. 3, which shows the gas pressure of the compressed gas driving the rotor increasing sharply and steadily in particular, so that the gas pressure reaches the maximum compressed gas value $p_{max}$ and retains it with any further increase in load (increasing torque).

The curves depicted as straight lines "A"-"D" and the ratio of the rotational speed, the gas pressure and the torque to one another are of course only examples; in particular the slopes of the straight lines "B"-"D" may be varied in any way as long as there is a reduction in the rotational speed on reaching a pressure value $p_2$ of the compressed gas which is lower than the maximum gas pressure $p_{max}$ of the compressed gas. Clearly the curves or the ratio of the rotational speed, the gas pressure and the torque to one another also need not be embodied as a straight line but instead may also be defined by non-steady curves or bent or kinked curves.

Figure 4:
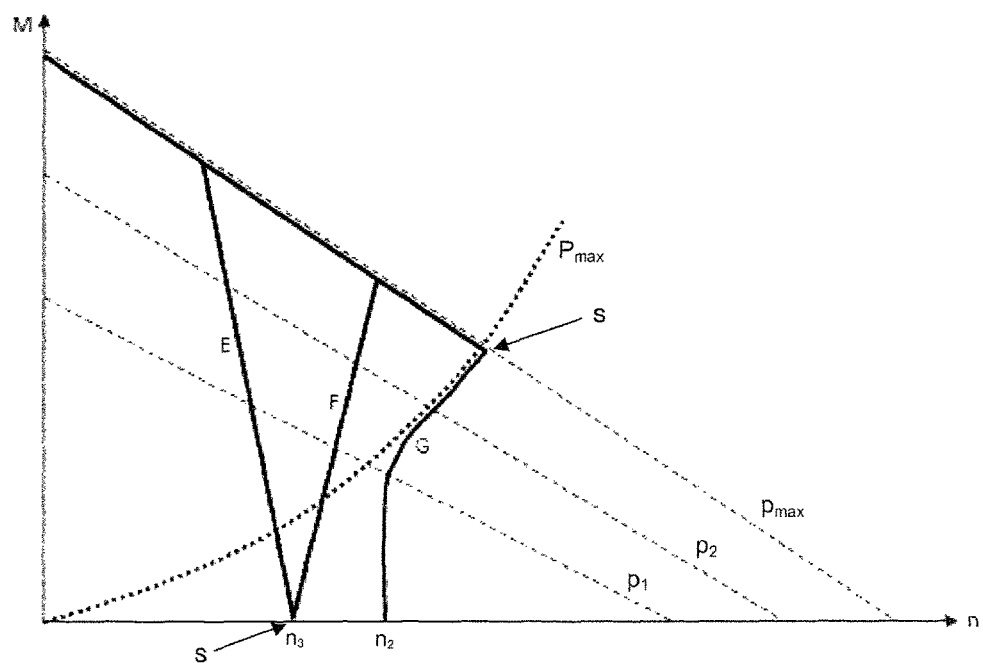

FIG. 4 shows a torque/rotational speed diagram of a second embodiment of a method for controlling and/or regulating a compressed-gas-operable medical or dental drive device with which (at the same time) the gas pressure of the compressed gas and the rotational speed of the rotor can be varied (in a controlled or regulated manner) by adjusting the valve on reaching a rotational speed limit value $n_2$, $n_3$ of the rotor (see in particular the curves from straight lines "E" and "F" of FIG. 4). The gas pressure of the compressed gas and the rotational speed of the rotor are preferably altered (at the same time) when, in addition to reaching a rotational speed limit value $n_2$, a pressure value $p_1$ of the compressed gas, which is lower than the maximum gas pressure $p_{max}$ of the compressed gas, is also achieved (see the curve "G" in FIG. 4). In particular the rotor may be operated at an essentially constant rotational speed $n_2$ before reaching the pressure value $p_1$. The rotational speed limit value $n_2$, $n_3$ may optionally be achievable in idling (with no load, see curves "E" and "F") or with a load (by applying a torque, see curve "G"). The rotational speed limit value $n_2$, $n_3$ or the combination of the rotational speed value $n_2$, $n_3$ and the pressure value $p_1$ thus define a switching point S, such that, when reached, the gas pressure of the compressed gas and the rotational speed of the rotor are altered (at the same time) when the load increases.

This method is preferably reversible so that if the rotational speed drops below the rotational speed limit value $n_2$, $n_3$ or optionally the pressure value is below the pressure value $p_h$ the drive device or the rotor is operated again with any other control method and/or regulating method, for example.

The straight lines "E" and "F" and the curve "G" shown here as well as the ratio of the rotational speed, the gas pressure and the torque to one another are of course merely examples, in particular with the slope being infinitely variable, for example. On reaching a rotational speed limit value $n_2$, $n_3$ and optionally the pressure value $p_h$ the following courses of the "E" and "F" straight lines and of the "G" curve, for example, or the ratios of the rotational speed, the gas pressure and the torque to one another are possible: the rotational speed (of the rotor) declines and the gas pressure of the compressed gas and the torque increase (see the "E" straight line). It is possible here that the gas pressure increases, so that the maximum gas pressure $p_{max}$ is reached and is optionally maintained with a further reduction in the rotational speed (see the "E" straight line), or alternatively, the maximum gas pressure $p_{max}$ is not reached. Alternatively, according to the straight line "F" and the curve "G," the rotational speed of the rotor, the gas pressure of the compressed gas and the torque all increase. The gas pressure of the compressed gas increases maximally until reaching the maximum gas pressure $p_{max}$ and if then the load (the torque) is further increased and then the rotational speed declines while retaining the maximum gas pressure $p_{max}$. In addition, it can be seen from the curve "G" that the increase in the gas pressure and in the rotational speed preferably follow the curve of the maximum power $P_{max}$ (corresponding to half the idling rotational speed) of the drive device.

Figure 5:
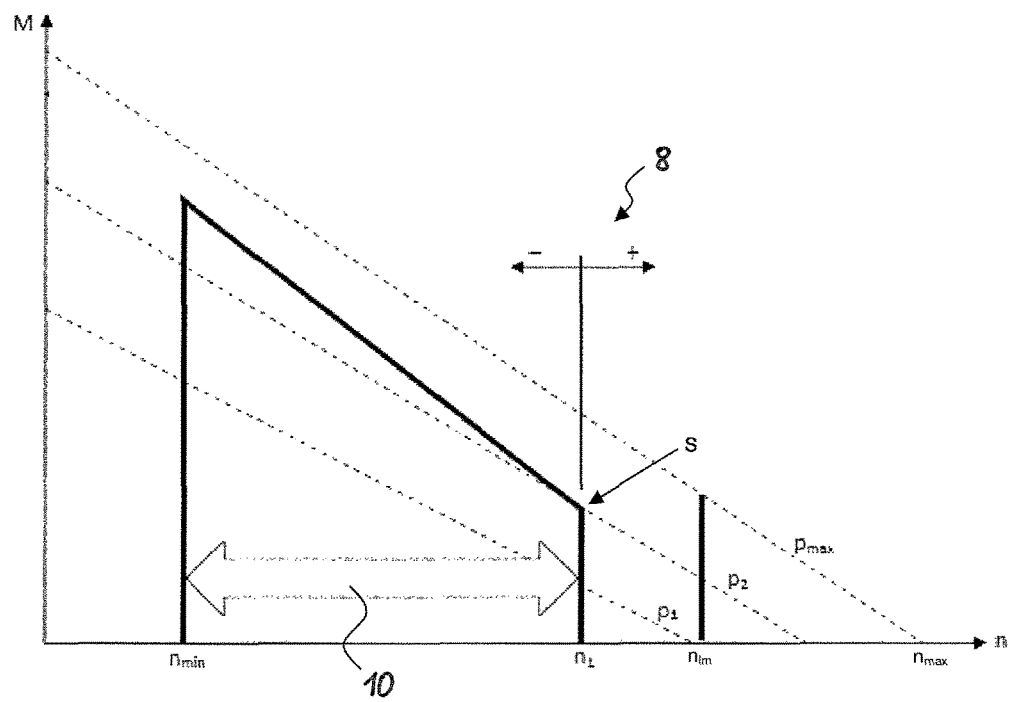
FIGS. 5-7 show different embodiments of control and/or regulating settings in the form of torque/rotational speed diagrams.

The torque/rotational speed diagram shown in FIG. 5 is an example of how a control and/or regulating characteristic described above can be combined with a control and/or regulating setting: a rotational speed $n_1$ defined as the setpoint rotational speed, preferably a minimum rotational speed or a lower limit of the rotational speed $n_{min}$ and preferably an upper limit of the rotational speed $n_{1m}$ are provided. The upper limit of the rotational speed $n_{1m}$ differs from the maximum rotational speed $n_{max}$, which is defined by the maximum gas pressure $p_{max}$ available to the drive device. The value of the upper limit of the rotational speed $n_{1m}$ is preferably lower than the value of the maximum rotational speed $n_{max}$ and limits the rotational speed of the rotor, for example, to protect the roller bearings supporting the rotor. The upper limit of the rotational speed $n_{1m}$ in particular defines a limit, which cannot be exceeded by the setpoint rotational speed $n_1$, which can be adjusted by the user (i.e., $n_1 < n_{1m}$ or $n_1 \leq n_{1m}$). The value of the setpoint rotational speed $n_1$ is preferably adjustable with an actuator element 8 (represented symbolically in FIG. 5) that can be operated by a user, for example, having a turn knob or a pushbutton by way of an operating device in particular with an actuator element that can be operated manually. The minimum rotational speed $n_{min}$ and the upper limit of the rotational speed $n_{1m}$ are preferably preset for the user in a manner that is not variable, but it is also conceivable for at least one of these two parameters to be variable by means of an actuator element that can be operated by a user, for example, by means of an operating device having a pushbutton or a turn knob.

As shown by the arrow 10 in FIG. 5, the user can set or adjust any desired value for the rotational speed during the operation of the drive device within the rotational speed limits $n_{min}$ and $n_{1m}$, preferably by means of an actuator element, which is different from the actuator element 8, in particular by means of an actuator element that can be operated by foot. On reaching the setpoint rotational speed $n_1$ and an increase in the torque, the rotational speed remains essentially constant (the setpoint rotational speed $n_1$ is kept essentially constant or a control and/or regulating device controls and/or regulates the system at this rotational speed, so that the rotor is operated at an essentially constant rotational speed), such that the gas pressure of the compressed gas increases. On reaching the switch point S, the rotational speed is reduced as described above for straight line "C" in FIG. 3. On reaching the lower limit of the rotational speed $n_{min}$, the supply of compressed gas to the drive device or to the rotor is suppressed.

It is of course possible to connect the control and/or regulating setting depicted in FIG. 5 to other control and/or regulating characteristics, in particular with the control and/or regulating characteristics "A," "B," D," "E," "F" or "G" depicted in FIGS. 3 and 4 or any other control and/or regulating characteristics.

A control and/or regulating device, in particular a microcontroller, is preferably provided which is designed to perform the control and/or regulating characteristic of FIG. 5. The control and/or regulating device is operatively connected to the actuator elements and at least one sensor, in particular a rotational speed sensor, and is also designed in particular to receive signals from the at least one sensor, to compare them with predefined values (for example, the setpoint rotational speed $n_1$, the upper limit of the rotational speed $n_{1m}$ or the lower limit of the rotational speed $n_{min}$) and to deliver a signal for adjusting the valve which acts on the compressed gas.

Figure 6:
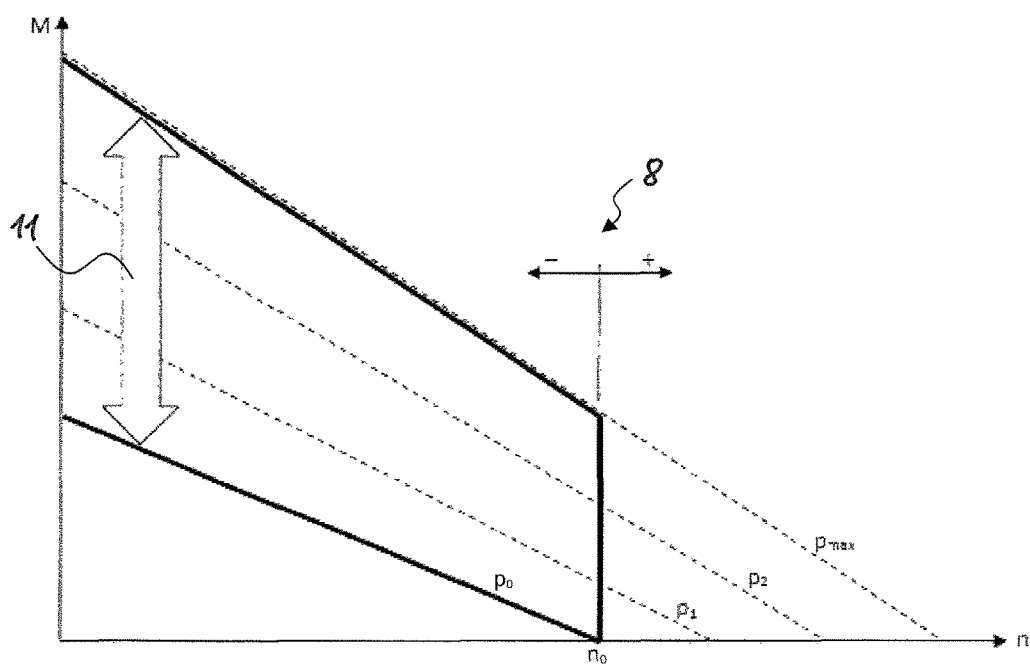

According to the control and/or regulating setting of FIG. 6, the user can set or adjust the torque or the gas pressure of the compressed gas at any desired level by means of an actuator element and/or an operating device, in particular with a foot-operated actuator element. According to this aspect, which may also be independent from any other embodiment described herein, a method for controlling and/or regulating a compressed-gas-operable medical, in particular dental, drive device with a rotor and a tool-holding device connected to the rotor is also provided, wherein the drive device can be supplied with compressed gas (at a maximum gas pressure) from a compressed gas source in order to induce a rotational movement of the rotor, and wherein the drive device has a valve for adjusting the gas pressure and/or the flow rate of the compressed gas, wherein the method is defined by the fact that the torque of the drive device or of the rotor or the gas pressure of the compressed gas driving the drive device or the rotor is provided as the variable to be controlled or regulated.

As illustrated by the arrow 11, the user can set or adjust any values for the torque or the gas pressure during the operation of the drive device within limits for the torque or gas pressure by using the foot control. The lower limit is labelled as $p_0$ in FIG. 6 and may be equal to or greater than 0 bar. The lower limit $p_0$ is either invariably predefined for the user or is adjustable by an actuator element that can be operated by the user, in particular by way of an operating device having a pushbutton or a turn knob, for example, preferably by means of a manually operable actuator element.

The upper limit is labelled as $p_{max}$ in FIG. 6 and equal to the maximum gas pressure available to the drive device or the rotor. Alternatively, the upper limit may be lower than the maximum gas pressure $p_{max}$. In the latter case, the upper limit is either predefined invariably for the user or is adjustable by an actuator element that can be operated by the user, in particular via an operating device with a pushbutton or a turn knob, for example, preferably by means of an actuator element that can be operated by hand.

The control and/or regulating setting of FIG. 6 additionally has a rotational speed limit value $n_0$. On reaching the rotational speed limit value $n_0$ and with an increase in load, the rotational speed remains essentially constant while the gas pressure increases. The rotational speed limit value $n_0$ is either predefined invariably for the user or is preferably adjustable by a user-operated actuator element 8, in particular via an operating device having a pushbutton or a turn knob, for example, preferably by means of a manually operable actuator element. In addition, a rotational speed lower limit $n_{min}$ that is variable by the user or is invariant and/or a rotational speed upper limit $n_{1m}$ may be provided, such that the rotational speed limit value $n_0$ cannot exceed the rotational speed upper limit as described in conjunction with FIG. 5.

In addition, the control and/or regulating setting depicted in FIG. 6 may preferably be associated with other control and/or regulating characteristics, in particular with the control and/or regulating characteristics "A" through "G" shown in FIGS. 3 and 4 or any other control and/or regulating characteristics.

A control and/or regulating device, in particular a microcontroller, which is designed to perform the control and/or regulating characteristics of FIG. 6 is preferably provided. The control and/or regulating device is operatively connected to the actuator elements and at least one sensor, in particular a device for determining the gas pressure of the compressed gas and/or a torque sensor and/or a rotational speed sensor and is also designed in particular to receive signals from the at least one sensor, to compare them with stipulated values (for example, a stipulated gas pressure value or a torque value, the setpoint rotational speed $n_1$, the rotational speed upper limit $n_{1m}$ or the rotational speed lower limit $n_{min}$) and to deliver a signal for adjusting the valve that adjusts the compressed gas.

Figure 7:
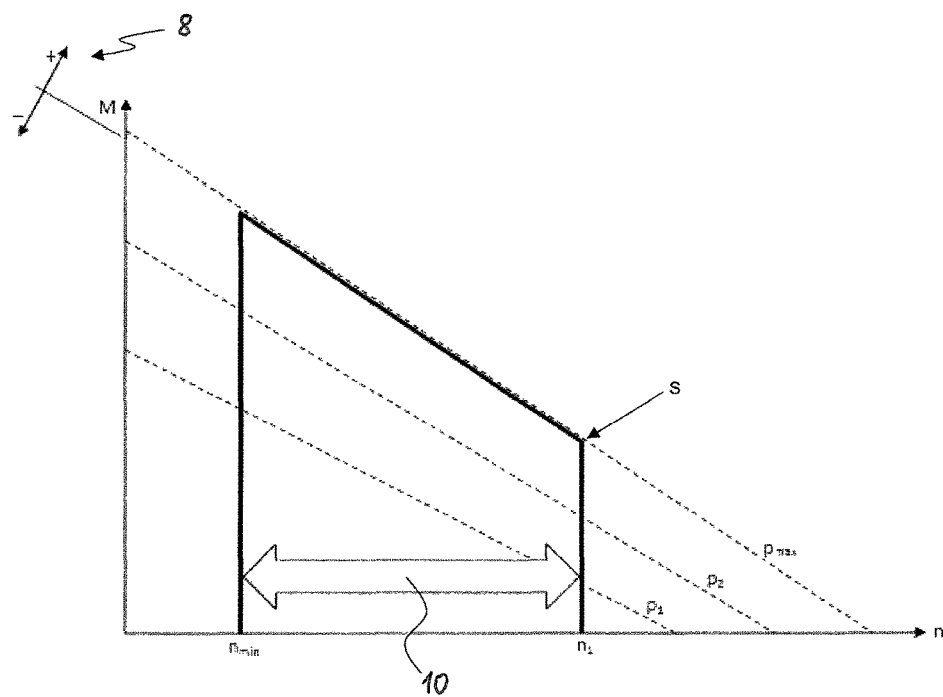

The torque/rotational speed diagram shown in FIG. 7 corresponds in most features to the diagram of FIG. 5, so that only the differences will be described below. The most important difference in this control and/or regulating setting is that a gas pressure limit value or an upper limit of the gas pressure of the compressed gas that drives the rotor is adjustable with an actuator element 8 that can be operated by hand. According to FIG. 7, the gas pressure limit value is equal to the maximum gas pressure $p_{max}$ available to the drive device or the rotor, but the gas pressure limit value can be reduced below the maximum gas pressure $p_{max}$ by operating the actuator element 8. It is of course also possible that, as described in conjunction with FIG. 5, the rotational speed $n_1$, which is also defined as the setpoint rotational speed, can be adjusted for the user by an actuator element.

Another difference in comparison with FIG. 5 is to be seen in the position of the switch point S which is selected so that the rotational speed is reduced essentially only on reaching the maximum gas pressure $p_{max}$.

Finally, in contrast with the embodiment in FIG. 5, no rotational speed upper limit $n_{1m}$ is provided.

Figure 8:
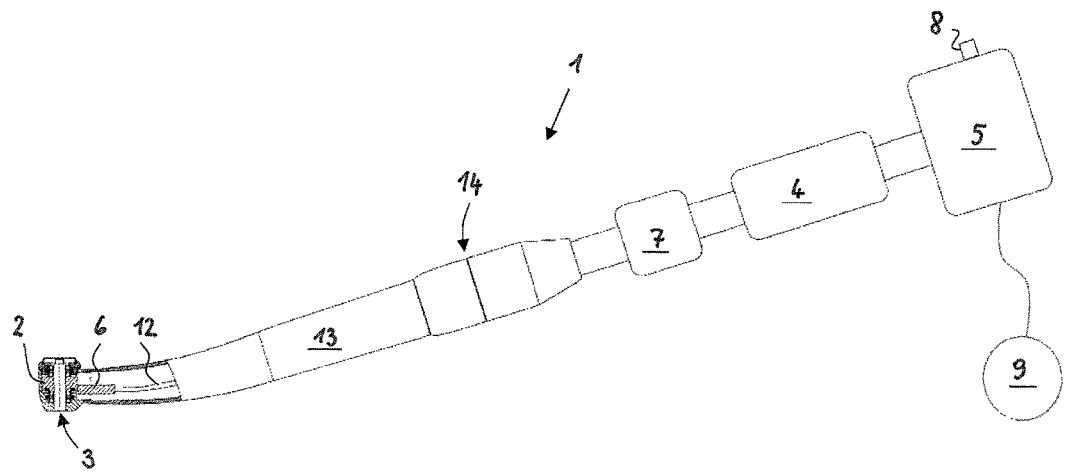
FIG. 8 shows a medical or dental compressed-gas-operable drive device for performing a method for controlling and/or regulating a compressed-gas-operable medical or dental drive device.

FIG. 8 shows a medical or dental drive device 1 comprising: a rotor 2 that can be set in motion by a compressed gas, a tool-holding device 3 which is connected to the rotor 2, a compressed gas line 12 for supplying compressed gas to the rotor 2, a rotational-speed-measuring device 6 for measuring the rotational speed of the rotor 2 and/or the tool-holding device 3, a valve 4 for adjusting the gas pressure and/or the flow rate of the compressed gas, preferably a device 7 for determining the gas pressure of the compressed gas and a control and/or regulating device 5, preferably with a microcontroller. The control and/or regulating device 5 is operatively connected to the rotational-speed-measuring device 6, to the device 7 for determining the gas pressure and to the valve 4, for example, by means of a supply tube or wirelessly connected so that the rotational speed measured data and the gas pressure measured data be transmitted to the control and/or regulating device 5 and the valve 4 can be operated by the control and/or regulating device 5 to adjust the gas pressure and/or the flow rate of the compressed gas on the basis of the rotational speed measured data transmitted and/or the gas pressure measured data. The control and/or regulating device 5 is designed in particular for performing at least one of the methods described above for controlling and/or regulating a compressed-gas-operable medical, in particular dental, drive device and/or for performing at least one of the control and/or regulating characteristics described above and/or for performing at least one of the control and/or regulating settings described above.

The drive device 1 preferably comprises a handpiece or contra-angle handpiece 13 that can be gripped by hand, at least the rotor or impeller 2, a part of the compressed gas line 12 and the tool-holding device 3 being provided therein. The handpiece or contra-angle handpiece 13 is preferably detachably connected to the control and/or regulating device 5 by a coupling device 14. In addition, the actuator element or the operating device 8 which is operable by hand by the user and the actuator element or the operating device 9 (foot control) that can be operated by the user by foot can also be connected to or be provided on the control and/or regulating device 5. The rotational-speed-measuring device 6 is preferably provided in the handpiece or the contra-angle handpiece 13 and comprises an inductive rotational speed sensor with a magnetic element attached to the rotor 2 or attached to a component rotating with the rotor 2.

A display for display of a parameter that is relevant for the control and/or regulation is preferably provided on the control and/or regulating device, for example, said parameter being at least one of the rotational speed, torque or gas pressure values mentioned above.

The present invention is not limited to the embodiments described here but instead includes all embodiments which employ or include the basic relevant function principle of the invention. In addition, all the features of all the embodiments that have been described and illustrated can be combined with one another.

What is claimed is:

1. A microcontroller-based method for controlling and/or regulating a compressed-gas-operable medical or dental drive device comprising a rotor and a tool-holding device connected to the rotor, wherein the drive device can be supplied with compressed gas at a maximum gas pressure from a compressed gas source to induce a rotational movement of the rotor and wherein the drive device comprises a valve for adjusting the gas pressure and/or a flow rate of the compressed gas, wherein the method comprises operating the rotor at a substantially constant rotational speed at least within a limited load range by adjusting the gas pressure and/or the flow rate of the compressed gas through the valve, directly or indirectly determining a pressure value of the compressed gas, and
reducing the rotational speed when the determined pressure value reaches a predetermined pressure value of the compressed gas which is lower than the maximum gas pressure of the compressed gas.

2. The method for controlling and/or regulating according to claim 1, wherein on reaching the predetermined pressure value of the compressed gas, which is lower than the maximum gas pressure of the compressed gas, the torque of the rotor is substantially constant or increases.

3. The method for controlling and/or regulating according to claim 1, wherein the predetermined pressure value is adjustable by a user.

4. The method controlling and/or regulating according to claim 1, wherein the value of the substantially constant rotational speed is adjustable by a user.

5. The method for controlling and/or regulating according to claim 1, comprising a rotational speed lower limit, below which the method for controlling and/or regulating is not performed, wherein the rotational speed lower limit is >0 s$^{-1}$.

6. A method for controlling and/or regulating a compressed-gas-operable medical or dental drive device comprising a rotor and a tool-holding device connected to the rotor, wherein the drive device can be supplied with compressed gas at a maximum gas pressure from a compressed gas source and wherein the drive device comprises a valve for adjusting the gas pressure and/or a flow rate of the compressed gas, wherein the method comprises:

measuring the rotational speed, directly or indirectly determining a pressure value of the compressed gas, and altering the gas pressure of the compressed gas and the rotational speed of the rotor by adjusting the valve when the measured rotational speed reaches a preset rotational speed limit and when the determined pressure value reaches a predetermined pressure value of the compressed gas which is lower than the maximum gas pressure of the compressed gas.

7. The method for controlling and/or regulating according to claim 6, wherein upon reaching the rotational speed limit value, the rotational speed of the rotor, the gas pressure of the compressed gas and the torque of the rotor increase.

8. The method for controlling and/or regulating according to claim 6, wherein upon reaching the rotational speed limit value, the rotational speed of the rotor decreases, and the gas pressure of the compressed gas and the torque of the rotor increase.

9. The method for controlling and/or regulating according to claim 6, wherein the rotational speed limit value and/or the predetermined pressure value is/are adjustable by a user.

10. The method for controlling and/or regulating according to claim 6, comprising a rotational speed lower limit, below which the method for controlling and/or regulating is not performed, wherein the rotational speed lower limit is >0 $s^{-1}$.

11. A microcontroller based method for controlling and/or regulating a compressed-gas-operable medical or dental drive device comprising a rotor and a tool-holding device connected to the rotor, a control and/or regulating device having a microcontroller, and a display, wherein the drive device can be supplied with compressed gas at a maximum gas pressure from a compressed gas source and wherein the drive device has a valve for adjusting a gas pressure and/or a flow rate of the compressed gas, wherein the method comprises, (i) when the drive device is not supplied with compressed gas, the user selecting a respective value of at least two of the following parameters through manually operating a single actuator element connected to the microcontroller at least within a predefined range: a rotational speed limit value of the rotor, which is lower than a maximum rotational speed determined by the maximum gas pressure, a setpoint rotational speed of the rotor, a gas pressure limit value of the compressed gas, which is lower than the maximum gas pressure, and/or a torque value, (ii) displaying the parameters selected by the user on the display and (iii) controlling and/or regulating a compressed-gas-operable medical or dental drive device through the microcontroller based on the parameters selected by the user.

12. A controlling and/or regulating device for a compressed-gas-operable medical or dental drive device having a rotor and a tool-holding device, the drive device being suppliable with compressed gas from a compressed gas source and having a valve for adjusting a gas pressure and/or a flow rate of the compressed gas, wherein the controlling and/or regulating device comprises a microcontroller which is configured to drive the rotor according to at least one control mode, wherein in a first control mode, the controlling and/or regulating device is configured to drive the rotor at a substantially constant rotational speed at least within a limited load range by adjusting the gas pressure and/or the flow rate of the compressed gas through the valve, to determine a pressure value of the compressed gas and to reduce the rotational speed of the rotor when the determined pressure value of the compressed gas reaches a predetermined pressure value of the compressed gas lower than a maximum gas pressure of the compressed gas, wherein in a second control mode, the controlling and/or regulating device is configured to drive the rotor, to determine the rotational speed of the rotor and a pressure value of the compressed gas and, to adjust the valve to alter the gas pressure of the compressed gas and the rotational speed of the rotor when the determined rotational speed reaches a preset rotational speed limit and when the determined pressure value reaches a predetermined pressure value of the compressed gas which is lower than the maximum gas pressure of the compressed gas, and wherein in a third control mode, the controlling and/or regulating device is configured to drive the rotor, according to user selected values of two parameters which are selected when the drive device is not supplied with compressed gas through manually operating one actuator element connected to the microcontroller and which are displayed on a display, wherein the parameters comprises at least two of: a rotational speed limit value of the rotor lower than a maximum rotational speed determined by the maximum gas pressure, a setpoint rotational speed of the rotor, a gas pressure limit value of the compressed gas lower than the maximum gas pressure and/or a torque value.

13. A medical or dental drive device, comprising a controlling and/or regulating device according to claim 12.

14. The medical or dental drive device according to claim 13, further comprising at least one actuator element operable by a user for setting at least one of the following parameters: a rotational speed limit value of the rotor which is lower than a maximum rotational speed determined by a maximum gas pressure, a setpoint rotational speed of the rotor, a gas pressure limit value of the compressed gas which is lower than the maximum gas pressure, or a torque value.

15. A compressed-gas-operable medical or dental drive device, comprising a rotor and a tool-holding device, a controlling and/or regulating device, wherein the drive device is suppliable with compressed gas from a compressed gas source and further comprises a valve for adjusting a gas pressure and/or a flow rate of the compressed gas, wherein the controlling and/or regulating device is configured to drive the rotor according to a third control mode in combination with a first control mode or a second control mode, wherein in the first control mode, the controlling and/or regulating device is configured to drive the rotor at a substantially constant rotational speed at least within a limited load range by adjusting the gas pressure and/or the flow rate of the compressed gas through the valve, to determine a pressure value of the compressed gas and to reduce the rotational speed of the rotor when the determined pressure value of the compressed gas reaches a predetermined pressure value of the compressed gas lower than a maximum gas pressure of the compressed gas, wherein in the second control mode, the controlling and/or regulating device is configured to drive the rotor, to determine the rotational speed of the rotor and a pressure value of the compressed gas and, to adjust the valve to alter the gas pressure of the compressed gas and the rotational speed of the rotor when the determined rotational speed reaches a preset rotational speed limit and when the determined pressure value reaches a predetermined pressure value of the compressed gas which is lower than the maximum gas pressure of the compressed gas, and wherein in the third control mode, the controlling and/or regulating device is configured to drive the rotor according to a user selected parameter which is selected when the drive device is not supplied with compressed gas, wherein the user selected parameter comprises at least one of a rotational speed limit value of the rotor lower than a maximum rotational speed determined by the maximum gas pressure, a setpoint rotational speed of the rotor, a gas pressure limit value of the compressed gas lower than the maximum gas pressure and/or a torque value, and a rotational-speed-measuring device for measuring the rotational speed of the rotor and/or of the tool-holding device, wherein the control and/or regulating device is operatively connected to rotational-speed-measuring device and to the valve, so that the measured data on the rotational speed can be transmitted to the control and/or regulating device, and the valve can be operated on the basis of transmitted measured data on the rotational speed by the control and/or regulating device for adjusting or altering the gas pressure and/or the flow rate of the compressed gas.

16. The medical or dental drive device according to claim 15, further comprising at least one actuator element operable by a user for setting at least one of the following parameters: a rotational speed limit value of the rotor which is lower than a maximum rotational speed determined by a maximum gas pressure, a setpoint rotational speed of the rotor, a gas pressure limit value of the compressed gas which is lower than the maximum gas pressure, or a torque value.

17. A medical or dental drive device comprising
a rotor and a tool-holding device,
a controlling and/or regulating device, wherein
the drive device is suppliable with compressed gas from a compressed gas source and further comprises a valve for adjusting a gas pressure and/or a flow rate of the compressed gas, wherein the controlling and/or regulating device is configured to drive the rotor according to at least one control mode, wherein in a first control mode, the controlling and/or regulating device is configured to drive the rotor at a substantially constant rotational speed at least within a limited load range by adjusting the gas pressure and/or the flow rate of the compressed gas through the valve, and to reduce the rotational speed of the rotor upon reaching a predetermined pressure value of the compressed gas lower than a maximum gas pressure of the compressed gas, wherein in a second control mode, the controlling and/or regulating device is configured to drive the rotor and, upon reaching a rotational speed limit, to adjust the valve to alter the gas pressure of the compressed gas and the rotational speed of the rotor, and wherein in a third control mode, the controlling and/or regulating device is configured to drive the rotor according to a user selected parameter which is selected when the drive device is not supplied with compressed gas, wherein the user selected parameter comprises at least one of a rotational speed limit value of the rotor lower than a maximum rotational speed determined by the maximum gas pressure, a setpoint rotational speed of the rotor, a gas pressure limit value of the compressed gas lower than the maximum gas pressure and/or a torque value, and a device for determining a gas pressure of the compressed gas, wherein the control and/or regulating device is operatively connected to the device for determining the gas pressure, so that measured data on the gas pressure can be transmitted to the control and/or regulating device, and the valve can be operated on the basis of the transmitted measured data on the gas pressure by the control and/or regulating device for adjusting the gas pressure and/or the flow rate of the compressed gas.

18. The medical or dental drive device according to claim 17, further comprising at least one actuator element operable by a user for setting at least one of the following parameters: a rotational speed limit value of the rotor which is lower than a maximum rotational speed determined by a maximum gas pressure, a setpoint rotational speed of the rotor, a gas pressure limit value of the compressed gas which is lower than the maximum gas pressure, or a torque value.

* * * * *